(12) United States Patent
Goto

(10) Patent No.: US 12,705,908 B2
(45) Date of Patent: Aug. 11, 2026

(54) MEDICAL IMAGE PROCESSING APPARATUS, ENDOSCOPE SYSTEM, MEDICAL IMAGE PROCESSING METHOD, AND MEDICAL IMAGE PROCESSING PROGRAM PROVIDING A NOTIFICATION IN ACCORDANCE WITH DRAWING INFORMATION

(71) Applicant: FUJIFILM Corporation, Tokyo (JP)

(72) Inventor: Misaki Goto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 227 days.

(21) Appl. No.: 18/463,271

(22) Filed: Sep. 7, 2023

(65) Prior Publication Data

US 2023/0419693 A1 Dec. 28, 2023

Related U.S. Application Data

(63) Continuation of application No. PCT/JP2022/009340, filed on Mar. 4, 2022.

(30) Foreign Application Priority Data

Mar. 9, 2021 (JP) ................................ 2021-037108

(51) Int. Cl.
*G06V 20/60* (2022.01)
*A61B 8/00* (2006.01)
(Continued)

(52) U.S. Cl.
CPC .............. *G06V 20/60* (2022.01); *A61B 8/085* (2013.01); *A61B 8/12* (2013.01); *A61B 8/5207* (2013.01);
(Continued)

(58) Field of Classification Search
CPC ............. G06V 20/60; G06V 2201/031; G06V 10/764; G06V 2201/03; A61B 8/085;
(Continued)

(56) References Cited

U.S. PATENT DOCUMENTS 11,918,176 B2 3/2024 Oosake et al.
2004/0239760 A1* 12/2004 Shoji ...................... G06T 11/60 348/E7.087
(Continued)

FOREIGN PATENT DOCUMENTS

CN 108596868 9/2018
CN 109410169 3/2019
(Continued)

OTHER PUBLICATIONS

"International Search Report (Form PCT/ISA/210) of PCT/JP2022/009340", mailed on May 17, 2022, with English translation thereof, pp. 1-5.
(Continued)

*Primary Examiner* — Andrew M Moyer
*Assistant Examiner* — Conor A O'Malley
(74) *Attorney, Agent, or Firm* — JCIPRNET

(57) ABSTRACT

A medical image processing apparatus according to an aspect of the present invention is a medical image processing apparatus including a processor. The processor is configured to execute an image acquisition process for sequentially acquiring time-series medical images; a drawing
(Continued)

information acquisition process for acquiring drawing information drawn in the medical images; a drawing information recognition process for recognizing the acquired drawing information; a target object recognition process for recognizing a target object from the medical images; a notification level determination process for determining a notification level for the target object by using the recognized drawing information; and a display process for causing a display device to display the target object at the determined notification level.

16 Claims, 9 Drawing Sheets

(51) Int. Cl.

| | |
|---|---|
| ***A61B 8/08*** | (2006.01) |
| ***A61B 8/12*** | (2006.01) |
| ***G06V 10/77*** | (2022.01) |
| ***G06V 20/50*** | (2022.01) |
| ***G16H 30/40*** | (2018.01) |

(52) U.S. Cl.
CPC .............. *G06V 10/77* (2022.01); *G06V 20/50* (2022.01); *G16H 30/40* (2018.01); *G06V 2201/031* (2022.01)

(58) Field of Classification Search
CPC ....... A61B 8/12; A61B 8/5207; A61B 8/5223; G16H 30/40; G16H 30/20; G16H 50/20; G06T 2207/10068; G06T 2207/10132; G06T 7/11
See application file for complete search history.

(56) References Cited

U.S. PATENT DOCUMENTS

| | | | |
|---|---|---|---|
| 2016/0242742 | A1 | 8/2016 | Gratacós Solsona et al. |
| 2020/0345324 | A1 | 11/2020 | Matsumoto et al. |
| 2021/0174557 | A1 | 6/2021 | Kamon |
| 2021/0209398 | A1 | 7/2021 | Endo |

FOREIGN PATENT DOCUMENTS

| | | | |
|---|---|---|---|
| JP | 2005007145 | 1/2005 | |
| JP | 2016531709 | 10/2016 | |
| WO | WO-2019123986 A1 * | 6/2019 | ............. G02B 23/24 |
| WO | 2019150715 | 8/2019 | |
| WO | 2020011569 | 1/2020 | |
| WO | 2020047204 | 3/2020 | |
| WO | 2020054541 | 3/2020 | |
| WO | 2020067100 | 4/2020 | |
| WO | 2020183770 | 9/2020 | |

OTHER PUBLICATIONS

"Written Opinion of the International Searching Authority (Form PCT/ISA/237) of PCT/JP2022/009340", mailed on May 17, 2022, with English translation thereof, pp. 1-7.
"Search Report of Europe Counterpart Application", issued on Aug. 7, 2024, p. 1-p. 10.
"Office Action of China Counterpart Application", issued on Decemeber 30, 2025, with English translation thereof, p. 1- p. 15.
Stephen Daniel Peterson, "Stereoscopic Label Placement—Reducing Distraction and Ambiguity in Visually Cluttered Displays", PhD Thesis, Visual Information Technology and Applications (VITA), Department of Science and Technology, Linkoping University, Feb. 19, 2020, pp. 1-85. Available at: https://www.diva-portal.org/smash/record.jsf?pid=diva2%3A277279&dswid=-4540.
"Office Action of Europe Counterpart Application", issued on Jun. 26, 2026, p. 1-p. 8.

* cited by examiner

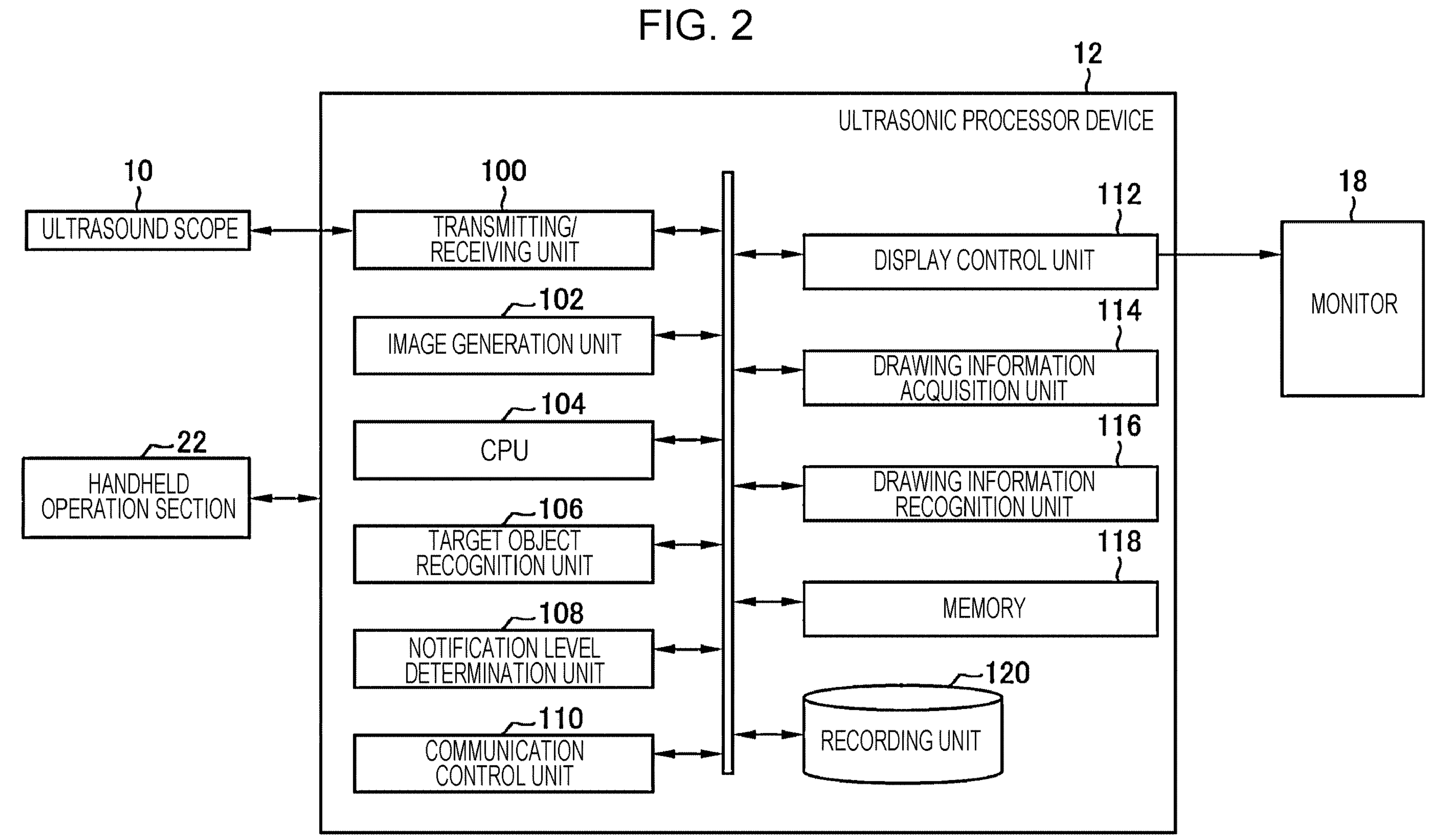
FIG. 2
12
ULTRASONIC PROCESSOR DEVICE
10
ULTRASOUND SCOPE
22
HANDHELD OPERATION SECTION
100
TRANSMITTING/ RECEIVING UNIT
102
IMAGE GENERATION UNIT
104
CPU
106
TARGET OBJECT RECOGNITION UNIT
108
NOTIFICATION LEVEL DETERMINATION UNIT
110
COMMUNICATION CONTROL UNIT
112
DISPLAY CONTROL UNIT
114
DRAWING INFORMATION ACQUISITION UNIT
116
DRAWING INFORMATION RECOGNITION UNIT
118
MEMORY
120
RECORDING UNIT
18
MONITOR FIG. 8A
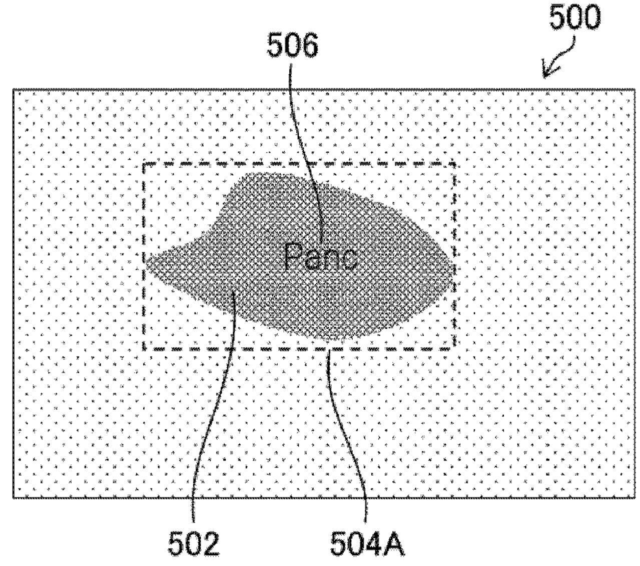
FIG. 8B
500
506
504B
Panc
504B
502
FIG. 8C
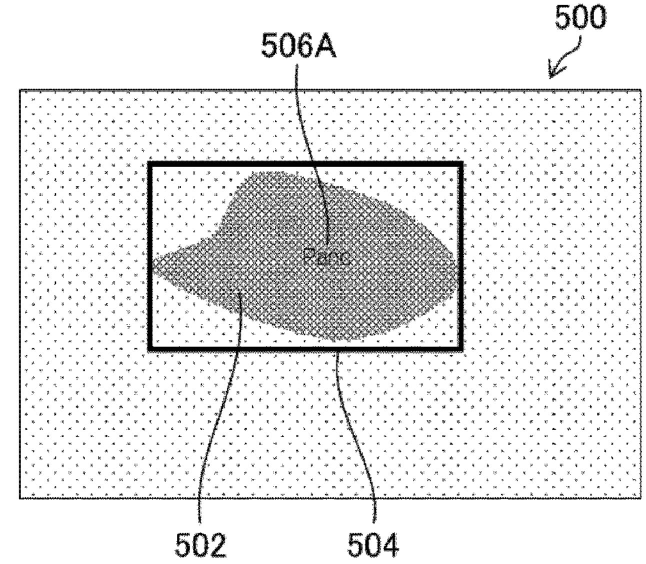

MEDICAL IMAGE PROCESSING APPARATUS, ENDOSCOPE SYSTEM, MEDICAL IMAGE PROCESSING METHOD, AND MEDICAL IMAGE PROCESSING PROGRAM PROVIDING A NOTIFICATION IN ACCORDANCE WITH DRAWING INFORMATION

CROSS-REFERENCE TO RELATED APPLICATIONS

The present application is a Continuation of PCT International Application No. PCT/JP2022/009340 filed on Mar. 4, 2022 claiming priority under 35 U.S.C § 119(a) to Japanese Patent Application No. 2021-037108 filed on Mar. 9, 2021. Each of the above applications is hereby expressly incorporated by reference, in its entirety, into the present application.

BACKGROUND OF THE INVENTION

1. Field of the Invention

The present invention relates to a medical image processing apparatus, an endoscope system, a medical image processing method, and a medical image processing program, and more specifically to a technique for providing a notification of a recognition result of a target object.

2. Description of the Related Art

It is known to notify a user such as a doctor of a region of interest detected by a medical image processing apparatus to assist the user in observing a medical image or making a diagnosis. For example, WO2020/054541A describes the control of the notification level for a recognized target object in accordance with the size thereof. For example, JP2005-007145A describes the drawing of a geometric shape, a symbol, a text, or the like in an endoscopic image.

SUMMARY OF THE INVENTION

During observation using a medical device such as an ultrasound device, a doctor may draw a geometric shape, a text, a measurement line, or the like in a medical image to measure the size of an organ or grasp the position of a lesion (information drawn in the way described above may be hereinafter referred to as "drawing information"). However, the drawn text, measurement line, or the like may adversely affect AI (Artificial Intelligence) recognition, for example, in diagnostic assistance with presentation (notification) of a recognition result of information (such as the presence or absence, position, or type) on a target object such as an organ or a lesion by using AI such as a trained model constructed by machine learning. As a result, an incorrect result may be output. However, the existing techniques as in WO2020/054541A and JP2005-007145A described above make it difficult to provide an appropriate notification in the depiction of drawing information.

The present invention has been made in view of such circumstances, and an object thereof is to provide a medical image processing apparatus, an endoscope system, a medical image processing method, and a medical image processing program that can provide an appropriate notification in accordance with drawing information.

To achieve the object described above, a medical image processing apparatus according to a first aspect of the present invention is a medical image processing apparatus including a processor, the processor being configured to execute an image acquisition process for sequentially acquiring time-series medical images, a drawing information acquisition process for acquiring drawing information drawn in the medical images, a drawing information recognition process for recognizing the acquired drawing information, a target object recognition process for recognizing a target object from the medical images, a notification level determination process for determining a notification level for the target object by using the recognized drawing information, and a display process for causing a display device to display the target object at the determined notification level.

As described above, if drawing information is drawn in a medical image, the reliability of a recognition result of a target object may be low. Accordingly, when providing a notification of a target object recognized from a medical image, the medical image processing apparatus according to the first aspect acquires and recognizes drawing information drawn in the medical image and determines a notification level for the target object by using the recognized drawing information. This makes it possible to provide an appropriate notification in accordance with the drawing information.

In the first aspect, the drawing information being "drawn in a medical image" may be the drawing information being embedded in the image (being part of the image and not being separable), or may be the drawing information being associated with the image but being separate information so as to be separable from the image (for example, the drawing information being a separate file from image data). The expression "recognizing the drawing information" may mean, for example, grasping the presence or absence of the drawing information, the quantity, position, size, shape, and the like of the drawing information in the medical image. The higher the "notification level" for the target object is, the more easily a user can recognize the target object. If a plurality of target objects are recognized in the medical image, the processor may be configured to determine a notification level for each of the target objects.

In the first aspect and the following aspects, the phrase "acquiring time-series medical images" includes sequentially acquiring a plurality of medical images captured at a determined frame rate. The acquisition may or may not be performed in real time. For example, medical images captured and recorded in advance may be acquired.

The medical image processing apparatus according to the first aspect can be implemented as, for example, a processor section of a medical image processing system, but is not limited to this aspect. The term "medical image" refers to an image obtained as a result of imaging, measurement, or the like of a living body such as a human body for the purpose of diagnosis, treatment, measurement, or the like. Examples of the medical image include an endoscopic image, an ultrasound image, a CT image (CT: Computed Tomography), and an MRI image (MRI: Magnetic Resonance Imaging). The medical image is also referred to as an image for medical use. In the first aspect and the following aspects, the term "target object" may be a "region of interest (ROI)" such as a lesion region, a candidate lesion region, an organ, a vessel, a region after treatment, or a treatment tool in a medical image. The "region of interest" may be referred to as an "interested region".

A medical image processing apparatus according to a second aspect is the medical image processing apparatus according to the first aspect, in which the processor is configured to, in response to the drawing information being recognized in the drawing information recognition process, reduce the notification level to be lower than a notification level when the drawing information is not recognized in the notification level determination process. This is because recognition of the drawing information may impair the reliability of the recognition result.

A medical image processing apparatus according to a third aspect is the medical image processing apparatus according to the first or second aspect, in which the processor is configured to, in the drawing information acquisition process, acquire the drawing information from a medical imaging apparatus connected to the medical image processing apparatus. The third aspect defines an aspect of a drawing information acquisition method. The medical imaging apparatus is, for example, an endoscope apparatus that captures an endoscopic image by using light or an ultrasound wave, or an ultrasound apparatus that acquires an ultrasound image by bringing an ultrasound probe into contact with a body surface of a subject.

A medical image processing apparatus according to a fourth aspect is the medical image processing apparatus according to any one of the first to third aspects, in which the processor is configured to, in the drawing information acquisition process, perform image processing on the medical images to acquire the drawing information. The fourth aspect defines another aspect of the drawing information acquisition method.

A medical image processing apparatus according to a fifth aspect is the medical image processing apparatus according to the fourth aspect, in which the processor is configured to, in the drawing information acquisition process, acquire the drawing information by using a trained model constructed by machine learning. The fifth aspect specifically defines a configuration for acquiring the drawing information. Examples of the trained model include a CNN (Convolutional Neural Network) and an SVM (Support Vector Machine).

A medical image processing apparatus according to a sixth aspect is the medical image processing apparatus according to any one of the first to fifth aspects, in which the processor is configured to check the medical images against drawable information that is drawable in the medical images to acquire the drawing information. Not every information is drawn in a medical image. The information to be drawn is limited to a certain extent depending on the type of the medical image, the body part of the subject, or the like. For this reason, as in the sixth aspect, a medical image is checked against drawable information (information that can be drawn in the medical image) to acquire accurate drawing information, thereby making it possible to provide a notification of the target object at an appropriate notification level.

A medical image processing apparatus according to a seventh aspect is the medical image processing apparatus according to any one of the first to sixth aspects, in which the processor is configured to, in the drawing information acquisition process, acquire information related to a geometric shape, a text, or a symbol drawn in the medical images as the drawing information. The seventh aspect defines a specific aspect of the drawing information.

A medical image processing apparatus according to an eighth aspect is the medical image processing apparatus according to the seventh aspect, in which the processor is configured to, in the drawing information acquisition process, acquire at least one of a position, a size, a shape, a line type, a color, or a type of at least one of the geometric shape, the text, or the symbol as the drawing information. The eighth aspect further specifically defines an aspect of the drawing information.

A medical image processing apparatus according to a ninth aspect is the medical image processing apparatus according to any one of the first to eighth aspects, in which the processor is configured to reduce the notification level for the target object to be lower than a notification level when the medical images do not have the drawing information, in accordance with a level of distinguishability of the drawing information. The "distinguishability" of the drawing information is the degree of influence of the drawing information on a recognition result of a target object and can depend on the type, number, amount, position, size, shape, and the like of the drawing information. Since high distinguishability may reduce the reliability of the recognition result, as in the ninth aspect, reducing the notification level for the target object in accordance with the level of distinguishability of the drawing information such that the notification level for the target object is lower than that when the medical images do not have the drawing information makes it possible to provide a notification of the target object at an appropriate notification level.

A medical image processing apparatus according to a tenth aspect is the medical image processing apparatus according to the ninth aspect, in which the processor is configured to reduce the notification level for a target object for which the distinguishability of the drawing information is recognized to be greater than or equal to a threshold value, such that the notification level is lower than a notification level when the medical images do not have the drawing information. The tenth aspect defines a standard for reducing the notification level for the target object.

A medical image processing apparatus according to an eleventh aspect is the medical image processing apparatus according to any one of the first to eighth aspects, in which the processor is configured to, in response to the drawing information being acquired in the drawing information acquisition process, reduce the notification level for the target object to be lower than a notification level when the medical images do not have the drawing information, regardless of a level of distinguishability of the drawing information.

A medical image processing apparatus according to a twelfth aspect is the medical image processing apparatus according to any one of the ninth to eleventh aspects, in which the processor is configured to determine the distinguishability in accordance with at least one of a position, a size, a shape, a line type, a color, or a type of a geometric shape, a text, or a symbol in the medical images. In the twelfth aspect, the processor may be configured to determine the level of distinguishability in consideration of the quantity of the geometric shape and the like.

A medical image processing apparatus according to a thirteenth aspect is the medical image processing apparatus according to any one of the first to twelfth aspects, in which the processor is configured to, in the notification level determination process, determine the notification level for the target object on the basis of a positional relationship between the target object and the drawing information in the medical images. For example, the processor can increase the notification level for the target object when the target object is far from the drawing information, and decrease the notification level for the target object when the target object is close to the drawing information.

To achieve the object described above, an endoscope system according to a fourteenth aspect of the present invention includes the medical image processing apparatus according to any one of the first to thirteenth aspects, an endoscope to be inserted into a subject, the endoscope including an imaging unit configured to sequentially capture the medical images; and the display device.

An endoscope system according to a fifteenth aspect is the endoscope system according to the fourteenth aspect, in which the endoscope is an ultrasonic endoscope configured to acquire ultrasound images of the subject as the medical images.

To achieve the object described above, a medical image processing method according to a sixteenth aspect of the present invention is a medical image processing method executed by a medical image processing apparatus including a processor, the medical image processing method including an image acquisition step of sequentially acquiring time-series medical images, a drawing information acquisition step of acquiring drawing information drawn in the medical images, a drawing information recognition step of recognizing the acquired drawing information, a target object recognition step of recognizing a target object from the medical images, a notification level determination step of determining a notification level for the target object by using the recognized drawing information, and a display step of causing a display device to display the target object at the determined notification level. According to the sixteenth aspect, as in the first aspect, it is possible to provide an appropriate notification in accordance with the drawing information. The medical image processing method according to the sixteenth aspect may further execute processing similar to that according to the second to thirteenth aspects.

To achieve the object described above, a medical image processing program according to a seventeenth aspect of the present invention is a medical image processing program for causing a medical image processing apparatus including a processor to execute a medical image processing method. The medical image processing method includes an image acquisition step of sequentially acquiring time-series medical images, a drawing information acquisition step of acquiring drawing information drawn in the medical images, a drawing information recognition step of recognizing the acquired drawing information, a target object recognition step of recognizing a target object from the medical images, a notification level determination step of determining a notification level for the target object by using the recognized drawing information, and a display step of causing a display device to display the target object at the determined notification level. According to the seventeenth aspect, as in the first aspect, it is possible to provide an appropriate notification in accordance with the drawing information. The medical image processing program according to the seventeenth aspect may be a program for further executing processing similar to that according to the second to thirteenth aspects. Aspects of the present invention can also provide a non-transitory recording medium storing the computer-readable code of the program according to this aspects.

As described above, a medical image processing apparatus, an endoscope system, a medical image processing method, and a medical image processing program according to the present invention can provide an appropriate notification in accordance with drawing information.

BRIEF DESCRIPTION OF THE DRAWINGS

FIG. 2 is a diagram illustrating a configuration of a main part of an ultrasonic processor device;

FIGS. 8A to 8C are views illustrating notification of the presence of a target object when drawing information is provided; and FIG. 9 is a view illustrating an example display in a case where a notification is provided at a notification level corresponding to a positional relationship between drawing information and a target object.

DESCRIPTION OF THE PREFERRED EMBODIMENTS

Embodiments of a medical image processing apparatus, an endoscope system, a medical image processing method, and a medical image processing program according to the present invention will be described hereinafter in detail with reference to the accompanying drawings.

Figure 1:
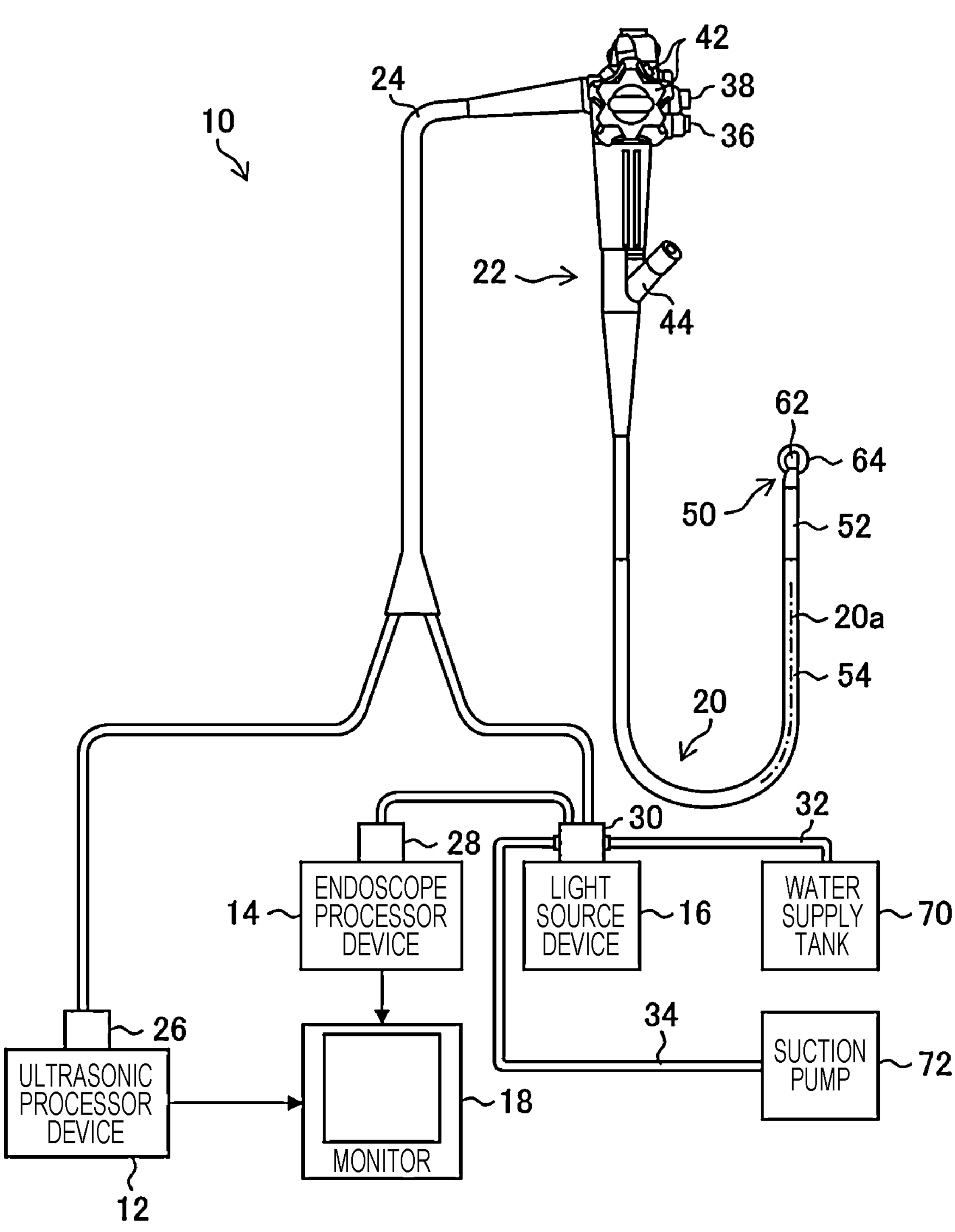
FIG. 1 is an external view of an endoscope system according to a first embodiment.

Overall Configuration of Endoscope System Including Medical Image Processing Apparatus FIG. 1 is an external view of an endoscope system. As illustrated in FIG. 1, an endoscope system 2 (endoscope system, medical imaging apparatus) includes an ultrasound scope 10 (endoscope, ultrasonic endoscope), an ultrasonic processor device 12 (medical image processing apparatus) that generates an ultrasound image, an endoscope processor device 14 (medical image processing apparatus) that generates an endoscopic image, a light source device 16 that supplies illumination light (observation light) to the ultrasound scope 10 to illuminate the inside of a body cavity, and a monitor 18 (display device) that displays the ultrasound image and the endoscopic image.

The ultrasound scope 10 includes an insertion section 20 to be inserted into a body cavity of a subject, a handheld operation section 22 coupled to a proximal end portion of the insertion section 20 and to be operated by an operator, and a universal cord 24 having one end connected to the handheld operation section 22. The other end of the universal cord 24 is provided with an ultrasonic connector 26 to be connected to the ultrasonic processor device 12, an endoscope connector 28 to be connected to the endoscope processor device 14, and a light source connector 30 to be connected to the light source device 16.

The ultrasound scope 10 is detachably connected to the ultrasonic processor device 12, the endoscope processor device 14, and the light source device 16 through these connectors. The light source connector 30 is also connected to an air/water supply tube 32 and a suction tube 34.

The light source device 16 is constituted by light sources for illumination (for example, a red light source, a green light source, a blue light source, and a violet light source that emit red, green, blue, and violet narrow-band light, respectively), a diaphragm, a condenser lens, a light source control unit, and so on, and these light sources can convert normal light (white light), special light (such as narrow-band light), and a combination thereof into observation light.

The monitor 18 receives respective video signals generated by the ultrasonic processor device 12 and the endoscope processor device 14 and displays an ultrasound image and an endoscopic image. The ultrasound image and the endoscopic image can be displayed such that only one of the images is appropriately switched and displayed on the monitor 18, or both of the images are simultaneously displayed.

The handheld operation section 22 is provided with an air/water supply button 36 and a suction button 38, which are arranged side by side, and is also provided with a pair of angle knobs 42 and a treatment tool insertion port 44.

The insertion section 20 has a distal end, a proximal end, and a longitudinal shaft 20*a*. The insertion section 20 is constituted by a tip main body 50, a bending part 52, and an elongated long flexible soft part 54 in this order from the distal end side of the insertion section 20. The tip main body 50 is formed by a hard member. The bending part 52 is coupled to the proximal end side of the tip main body 50. The soft part 54 couples the proximal end side of the bending part 52 to the distal end side of the handheld operation section 22. That is, the tip main body 50 is disposed on the distal end side of the insertion section 20 near the longitudinal shaft 20*a*. The bending part 52 is remotely operated to bend by turning the pair of angle knobs 42 disposed in the handheld operation section 22. As a result, the user can direct the tip main body 50 in a desired direction.

The tip main body 50 is attached with an ultrasound probe 62 (imaging unit) and a bag-like balloon 64 that covers the ultrasound probe 62. The balloon 64 can expand or contract when water is supplied from a water supply tank 70 or the water in the balloon 64 is sucked by a suction pump 72. The balloon 64 is inflated until the balloon 64 abuts against the inner wall of the body cavity to prevent attenuation of an ultrasound wave and an ultrasound echo (echo signal) during ultrasound observation.

The tip main body 50 is also attached with an endoscopic observation portion (not illustrated) having an illumination portion and an observation portion including an objective lens, an imaging element, and so on. The endoscopic observation portion is disposed behind the ultrasound probe 62 (on the handheld operation section 22 side).

With the configuration described above, the endoscope system 2 can sequentially acquire (sequentially capture) endoscopic images (optical images) and ultrasound images. The endoscope system 2 may acquire endoscopic images or ultrasound images from a recording unit 120 or a server or a database (not illustrated).

Medical Image Processing Apparatus

FIG. 2 is a block diagram illustrating a configuration of a main part of an ultrasonic processor device serving as a medical image processing apparatus according to the present invention.

The ultrasonic processor device 12 (medical image processing apparatus; processor) illustrated in FIG. 2 is a device that recognizes a region of interest (target object) in a medical image on the basis of sequentially acquired time-series medical images and causes a display device to display the target object at a notification level corresponding to drawing information. The ultrasonic processor device 12 is constituted by a transmitting/receiving unit 100 (processor; image acquisition unit), an image generation unit 102 (processor; image acquisition unit), a CPU 104 (processor; CPU: Central Processing Unit), a target object recognition unit 106 (processor; target object recognition unit), a notification level determination unit 108 (processor; notification level determination unit), a communication control unit 110 (processor), a display control unit 112 (processor; display unit), a drawing information acquisition unit 114 (processor; drawing information acquisition unit), a drawing information recognition unit 116 (processor; drawing information recognition unit), a memory 118, and the recording unit 120 (recording device). The processing of each of these components is implemented by one or more processors, as described below.

The CPU 104 operates in accordance with various programs stored in the memory 118 and including a medical image processing program according to the present invention to perform overall control of the target object recognition unit 106, the notification level determination unit 108, the display control unit 112, the drawing information acquisition unit 114, and the drawing information recognition unit 116, and serves as some of these components. The memory 118 includes a non-transitory recording medium such as a ROM (ROM: Read Only Memory) on which the medical image processing program and so on are recorded, and a transitory recording medium such as a RAM (RAM: Random Access Memory) used as a transitory storage area.

The transmitting/receiving unit 100 and the image generation unit 102, which serve as an image acquisition unit, sequentially acquire time-series medical images (image acquisition process, image acquisition step).

A transmitting unit of the transmitting/receiving unit 100 generates a plurality of drive signals to be applied to a plurality of ultrasonic transducers of the ultrasound probe 62 of the ultrasound scope 10, and assigns respective delay times to the plurality of drive signals on the basis of a transmission delay pattern selected by a scan control unit (not illustrated) before applying the plurality of drive signals to the plurality of ultrasonic transducers.

A receiving unit of the transmitting/receiving unit 100 amplifies a plurality of detection signals, each of which is output from one of the plurality of ultrasonic transducers of the ultrasound probe 62, and converts the detection signals from analog detection signals to digital detection signals (also referred to as RF (Radio Frequency) data). The RF data is input to the image generation unit 102.

The image generation unit 102 assigns respective delay times to the plurality of detection signals represented by the RF data on the basis of a reception delay pattern selected by the scan control unit and adds the detection signals together to perform reception focus processing. Through the reception focus processing, sound ray data in which the focus of the ultrasound echo is narrowed is formed.

The image generation unit 102 corrects the sound ray data for attenuation caused by the distance in accordance with the depth of the reflection position of the ultrasound wave by using STC (Sensitivity Time Control), and then performs envelope detection processing on the sound ray data by using a low pass filter or the like to generate envelope data. The image generation unit 102 stores envelope data for one frame or more preferably for a plurality of frames in a cine memory (not illustrated). The image generation unit 102 performs pre-process processing, such as Log (logarithmic) compression and gain adjustment, on the envelope data stored in the cine memory to generate a B-mode image.

In this way, the transmitting/receiving unit 100 and the image generation unit 102 sequentially acquire time-series B-mode images (hereafter referred to as "medical images").

The target object recognition unit 106 performs a process (detection process, target object recognition process, or target object recognition step) of recognizing information related to the position of a target object (region of interest) in a medical image on the basis of the medical images and a process (classification process, classification step) of classifying the target object into a class among a plurality of classes on the basis of the medical image. For example, the target object recognition unit 106 can be configured using a trained model constructed by machine learning (a model trained by using an image set constituted by captured images of a living body), such as a CNN (Convolutional Neural Network) or an SVM (Support Vector Machine), for example. In the present embodiment, the target object is, for example, a region of interest such as an organ or a blood vessel in a medical image (a tomographic image of a B-mode image), and examples of the target object include the pancreas, the main pancreatic duct, the spleen, the splenic vein, the splenic artery, and the gallbladder.

An example of a layer configuration in a case where the target object recognition unit 106 is constituted by a CNN will be described. The CNN includes an input layer, an intermediate layer, and an output layer. The input layer receives a medical image generated by the image generation unit 102 and outputs a feature value. The intermediate layer includes convolution layers and pooling layers and receives the feature value output from the input layer to calculate another feature value. These layers have a structure in which a plurality of "nodes" are connected by "edges", and hold a plurality of weight parameters. The values of the weight parameters change as learning progresses. The output layer recognizes a target object (region of interest) appearing in the input medical image on the basis of the feature value output from the intermediate layer and outputs a recognition result.

In this example, when sequentially receiving time-series medical images, the target object recognition unit 106 recognizes (detects) the position of a region of interest in each of the received medical images, outputs information related to the position, recognizes (classifies) a class to which the region of interest belongs among a plurality of classes, and outputs information (class information) indicating the recognized class.

The target object recognition unit 106 is capable of setting, for example, the center position of a rectangular shape surrounding the region of interest as the position of the region of interest. In the present embodiment, information indicating the type of organ or blood vessel can be referred to as "class information".

The drawing information acquisition unit 114 (processor, drawing information acquisition unit) acquires drawing information drawn in the medical image. The drawing information acquisition unit 114 may acquire the drawing information by performing image processing, may acquire the drawing information from another medical imaging apparatus connected to the endoscope system 2, or may acquire the drawing information by checking the medical image against drawable information. The drawing information may be acquired by using these means in combination. When acquiring the drawing information by performing image processing, the drawing information acquisition unit 114 may use a trained model (such as a CNN or an SVM) constructed by machine learning. The drawing information recognition unit 116 recognizes the drawing information, and the notification level determination unit 108 determines a notification level for the target object by using the recognized drawing information.

The display control unit 112 causes the monitor 18 (display device) to display the time-series medical images (endoscopic images, ultrasound images) sequentially acquired by the transmitting/receiving unit 100 and the image generation unit 102. In this example, a moving image indicating an ultrasound tomographic image is displayed on the monitor 18. The display control unit 112 further causes the monitor 18 to display the target object at the notification level determined by the notification level determination unit 108.

Medical image processing with the functions described above will be described in detail below.

Implementation of Functions by Various Processors

The functions of the ultrasonic processor device 12 described above can be implemented using various processors and a recording medium. The various processors include, for example, a CPU (Central Processing Unit), which is a general-purpose processor that executes software (program) to implement various functions. The various processors described above also include a GPU (Graphics Processing Unit), which is a processor specialized for image processing, and a programmable logic device (PLD) such as an FPGA (Field Programmable Gate Array), which is a processor whose circuit configuration is changeable after manufacture. A configuration using a GPU is effective for the processing of images as in the present invention. Further, a dedicated electric circuit or the like, which is a processor having a circuit configuration designed specifically for executing specific processing, such as an ASIC (Application Specific Integrated Circuit), is also included in the "various processors" described above.

The function of each component may be implemented by one processor or may be implemented by a plurality of processors of the same type or different types (for example, a plurality of FPGAs, a combination of a CPU and an FPGA, or a combination of a CPU and a GPU). Alternatively, a plurality of functions may be implemented by one processor. Examples of configuring a plurality of functions by a single processor include, first, a form in which, as typified by a computer, the single processor is configured by a combination of one or more CPUs and software and the processor is implemented as the plurality of functions. The examples include, second, a form in which, as typified by a system on chip (SoC) or the like, a processor is used in which the functions of the entire system are implemented by a single IC (Integrated Circuit) chip. As described above, the various functions are configured using one or more of the various processors described above as a hardware structure. More specifically, the hardware structure of the various processors is an electric circuit (circuitry) including a combination of circuit elements such as semiconductor elements. These electric circuit may be an electric circuit that implements the functions described above by using logical OR, logical AND, logical NOT, exclusive OR, and logical operation as a combination thereof.

When the processor or electric circuit described above executes software (program), the code of the software to be executed, which is readable by a computer (for example, various processors or electric circuits constituting the ultrasonic processor device 12, and/or a combination thereof), is stored in a non-transitory recording medium such as a ROM (Read Only Memory), and the computer refers to the software. The software stored in the non-transitory recording medium includes a medical image processing program for executing a medical image processing method according to the present invention, and data used for the execution (such as data used to set a display form and a notification form, and weight parameters used in the target object recognition unit 106). The code may be recorded in a non-transitory recording medium such as various magneto-optical recording devices or a semiconductor memory, instead of the ROM. At the time of processing using software, for example, a RAM (RAM: Random Access Memory, memory) is used as a temporary storage area, and, for example, data stored in an EEPROM (Electronically Erasable and Programmable Read Only Memory) (not illustrated) can also be referred to. The "non-transitory recording medium" may be the memory 118 or the recording unit 120.

The recording unit 120 has recorded thereon an ultrasound image and an endoscopic image (medical image), drawing information, a detection result of a target object, processing conditions (conditions for detection and providing a notification), and so on. Other information may also be recorded. The communication control unit 110 performs control to acquire a medical image and the like from another medical imaging apparatus connected to the endoscope system 2, an external server, or a database.

Overview of Medical Image Processing

Figure 3:
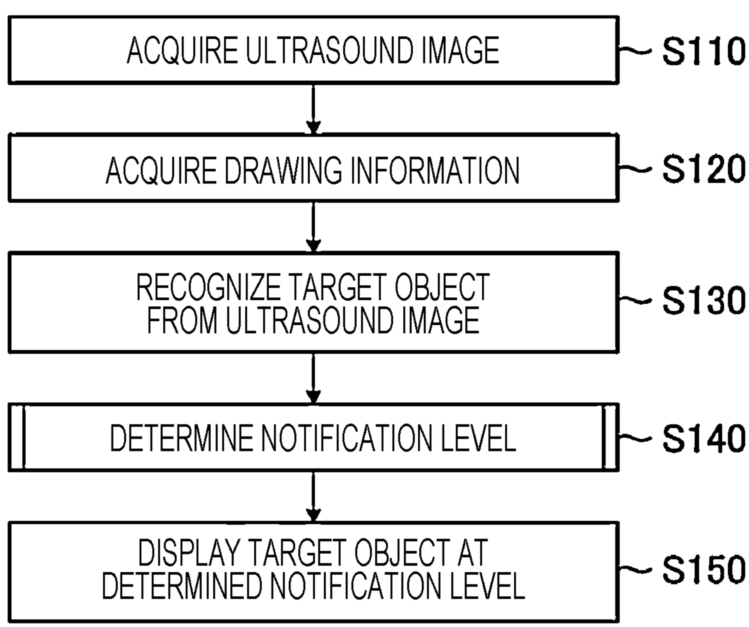
FIG. 3 is a flowchart illustrating an overview of a medical image processing method according to the first embodiment.

Medical image processing performed in the endoscope system 2 having the configuration described above (execution of a medical image processing method and a medical image processing program according to the present invention) will be described. FIG. 3 is a flowchart illustrating an overview of a medical image processing method according to a first embodiment. The procedures described below may be executed in a different order as necessary.

The transmitting/receiving unit 100 and the image generation unit 102 sequentially acquire time-series ultrasound images (medical images) (step S110: image acquisition process, image acquisition step). The drawing information acquisition unit 114 acquires drawing information drawn in an ultrasound image (step S120: drawing information acquisition process, drawing information acquisition step). The drawing information acquisition unit 114 acquires, as drawing information, information on a geometric shape, a text, or a symbol drawn in an ultrasound image (for example, at least one of the position, size, shape, line type, color, or type of at least one of the geometric shape, the text, or the symbol). The drawing information acquisition unit 114 may acquire drawing information from a medical imaging apparatus connected to the endoscope system 2, may acquire drawing information by using a trained model constructed by machine learning, or may acquire drawing information by checking the ultrasound image against drawable information (information drawable in the ultrasound image, which is a medical image). The drawable information is, for example, a character string that can be drawn (such as the name or abbreviation of an organ or a vessel, e.g., "Pancreas" or "SV", or a comment given by an image interpreter), the type of symbol (such as an arrow, a circle, an ellipse, or a curve having an indefinite shape), or a feature of a measurement line or the like (such as a broken-line or solid-line measurement line). The drawing information acquisition unit 114 may use a plurality of these means to acquire drawing information.

Figure 4A:
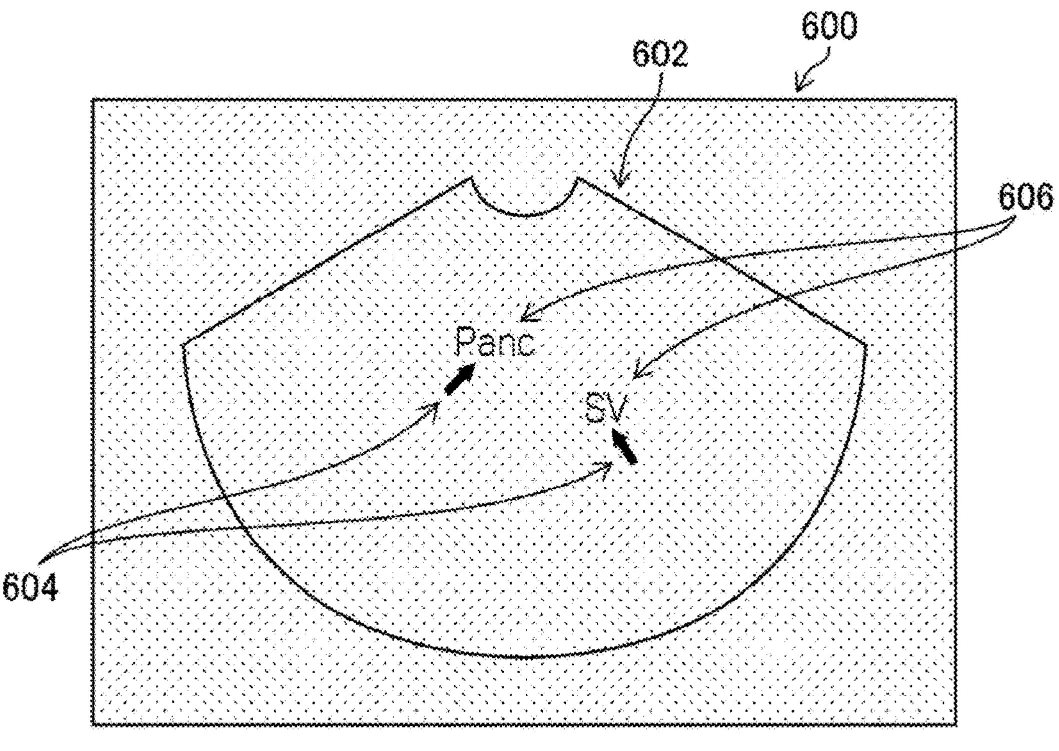
FIGS. 4A and 4B are views illustrating examples of drawing information.
Figure 4B:
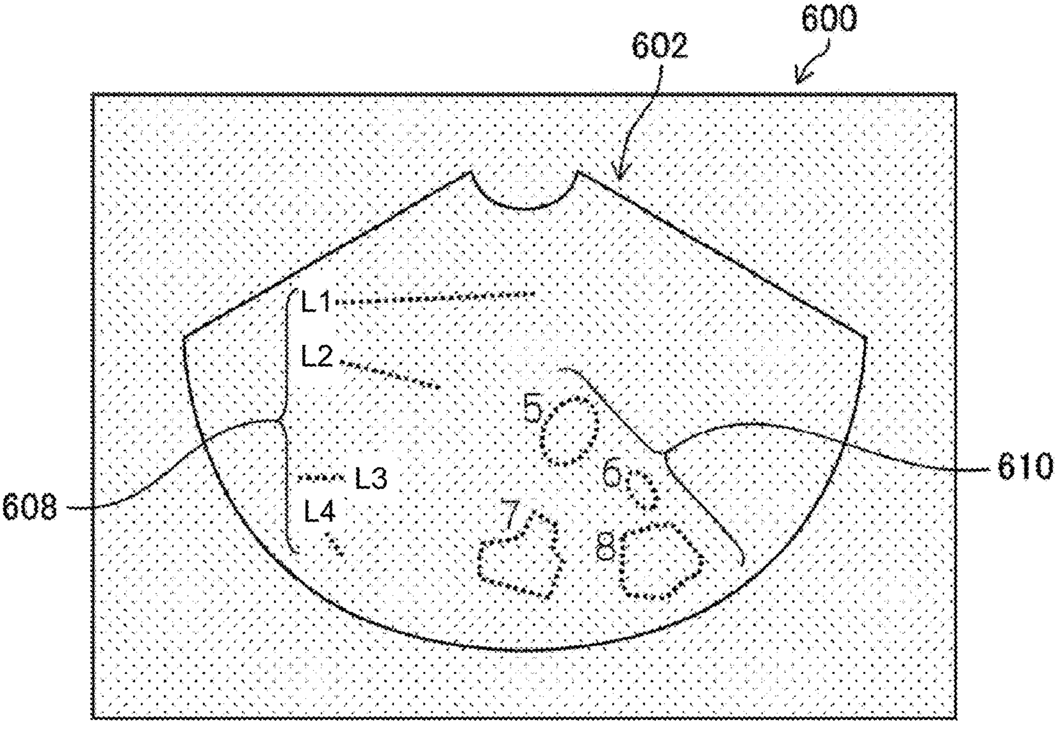

FIGS. 4A and 4B are views illustrating examples of drawing information, and a screen 600 of the monitor 18 displays an ultrasound image 602 (FIGS. 4A and 4B does not illustrate a target object to clearly indicate the drawing information). In the example illustrated in FIG. 4A, arrows 604 (drawing information), which are one aspect of a symbol, and character strings 606 (drawing information), which are one aspect of a text, are drawn in the ultrasound image 602. The text "Panc" is an abbreviation for "pancreas" and means the pancreas, and the text "SV" is an abbreviation for "splenic vein" and means the splenic vein. In the example illustrated in FIG. 4B, by contrast, measurement lines 608 and measurement shapes 610, which are one aspect of a geometric shape, are drawn in the ultrasound image 602.

The target object recognition unit 106 recognizes a target object (step S130: target object recognition process, target object recognition step). The notification level determination unit 108 determines a notification level for the target object by using the recognized drawing information (step S140: notification level determination process, notification level determination step). Details of the processing of step S140 will be described below. The display control unit 112 causes the monitor 18 (display device) to display the target object at the determined notification level (step S150: display process, display step).

Figure 5:
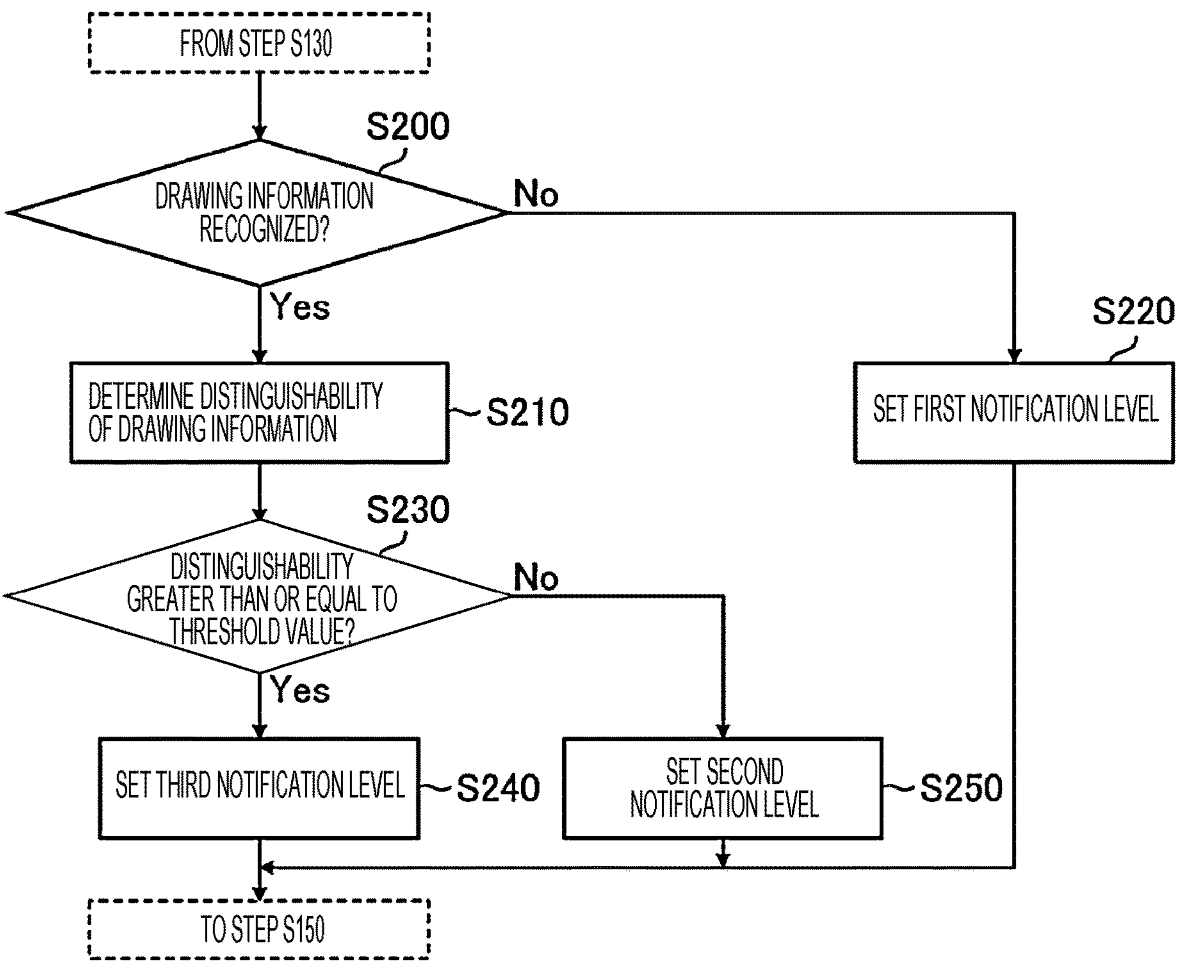
FIG. 5 is a flowchart illustrating details of a notification level determination process.

Details of Notification Level Determination Process/Notification Level Determination Step FIG. 5 is a flowchart illustrating details of the notification level determination process/notification level determination step in step S140 in FIG. 3. The drawing information recognition unit 116 (processor) determines whether drawing information has been recognized in the drawing information (acquired in step S120) (step S200: drawing information recognition process/drawing information recognition step). The expression "recognizing drawing information" refers to, for example, grasping the presence or absence of drawing information and the content thereof, and the "content of drawing information" includes, for example, at least one of the position, size, shape, line type, color, or type of at least one of a geometric shape, a text, or a symbol such as the arrows 604 or the character strings 606 described above. Preferably, the drawing information recognition unit 116 further grasps the quantity of the drawing information and the positional relationship between the target object and the drawing information.

If the drawing information recognition unit 116 does not recognize drawing information (if no drawing information is present), the determination of step S200 is negative, and the notification level determination unit 108 (processor) sets a first notification level as the notification level for the target object (step S220: notification level determination process, notification level determination step).

If the drawing information recognition unit 116 recognizes any drawing information (if drawing information is present), the determination of step S200 is affirmative, and the notification level determination unit 108 reduces the notification level for the target object to be lower than the first notification level (a case where the medical image has no drawing information), regardless of the level of distinguishability of the drawing information. Specifically, the notification level determination unit 108 determines the distinguishability of the drawing information (step S210: notification level determination process, notification level determination step), and reduces the notification level for the target object to be lower than the first notification level (a notification level in a case where the medical image has no drawing information) in accordance with the level of distinguishability. More specifically, the notification level determination unit 108 determines whether the distinguishability of the drawing information is greater than or equal to a threshold value (step S230: notification level determination process, notification level determination step). If the determination is affirmative, the notification level determination unit 108 sets a third notification level as the notification level for the target object (step S240: notification level determination process, notification level determination step). If the determination is negative, the notification level determination unit 108 sets a second notification level as the notification level for the target object (step S250: notification level determination process, notification level determination step).

Figure 6:
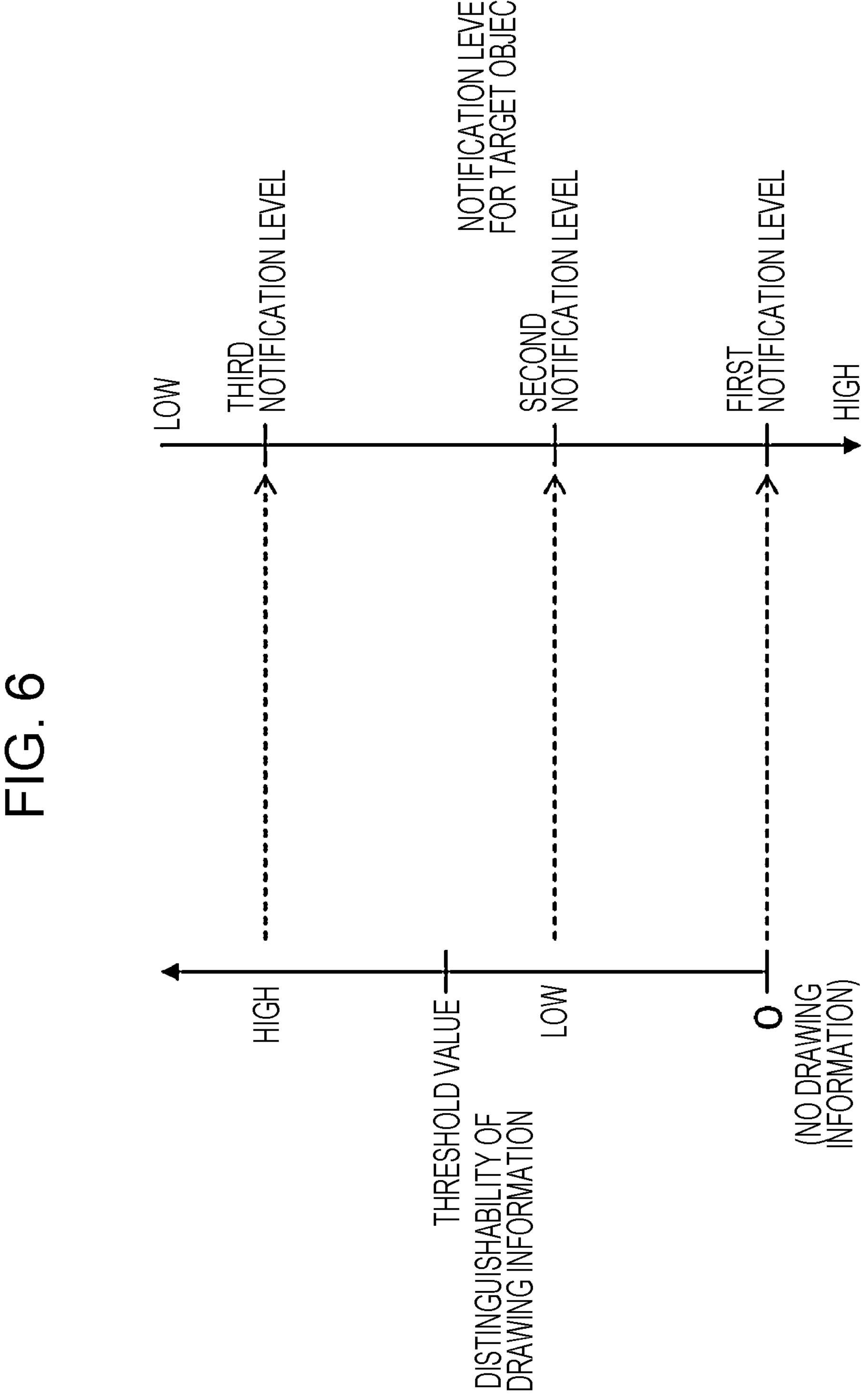
FIG. 6 is a diagram illustrating a relationship between levels of distinguishability of drawing information and notification levels for a target object.

FIG. 6 is a diagram illustrating a relationship between levels of distinguishability of drawing information and notification levels for a target object. The left-hand portion of FIG. 6 illustrates the levels of distinguishability of the drawing information, and the level of distinguishability at the bottom of FIG. 6 is zero (when no drawing information is present), with levels of distinguishability increasing toward the top. By contrast, the right-hand portion of FIG. 6 illustrates the notification levels for the target object, with notification levels increasing toward the bottom of FIG. 6. As illustrated in FIG. 6, the notification level in a case where the distinguishability of the drawing information is zero (no drawing information) is a "first notification level", the notification level in a case where the distinguishability is less than a threshold value is a "second notification level", and the notification level in a case where the distinguishability is greater than or equal to the threshold value is a "third notification level".

The "distinguishability" of the drawing information can be considered to be the degree of influence of the drawing information on a recognition result of a target object, and can depend on the type, number, amount, position, size, shape, distance to the target object, or the like of the drawing information. Since high distinguishability may reduce the reliability of the recognition result, as described above, the notification level for the target object is determined in accordance with the distinguishability, thereby making it possible to provide an appropriate notification in accordance with the drawing information.

Example of Displaying Target Object at Determined Notification Level

Figure 7:
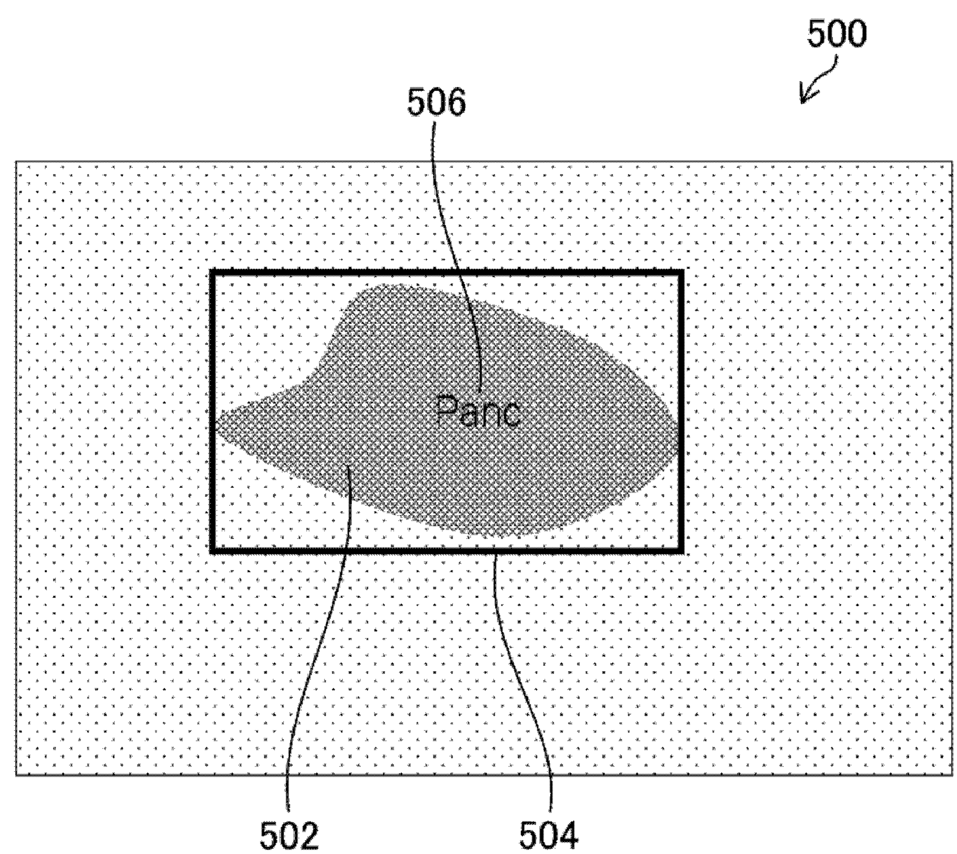
FIG. 7 is a view illustrating notification of the presence of a target object when no drawing information is provided.

An example of displaying a target object at a notification level determined by the process described above will be described. FIG. 7 is a view illustrating an example of display in the absence of drawing information (the distinguishability of the drawing information is zero; an example of display at the first notification level), and an ultrasound image 500 includes a region of interest 502 (target object; in this example, the pancreas). The display control unit 112 provides a notification of the position and type of the region of interest 502 by using a bounding box 504 and a character string 506.

FIGS. 8A to 8C are views illustrating examples of display in the presence of drawing information, and illustrates an example in which the notification level is reduced compared with that in the example in FIG. 7 (examples of display at the second notification level or the third notification level). In the example illustrated in FIG. 8A, the display control unit 112 displays a bounding box 504A with thinner broken lines than the bounding box 504 (by changing the line thickness and the line type). In the example illustrated in FIG. 8B, the display control unit 112 displays a bounding box 504B such that only the corner portions thereof are visible. In the example illustrated in FIG. 8C, the display control unit 112 displays a character string 506A in a reduced size (the character string may be represented by an initial or an abbreviation). The forms illustrated in FIGS. 8A to 8C may be used in combination. Alternatively, the color or brightness of the bounding box or the character string may be changed.

Figure 9:
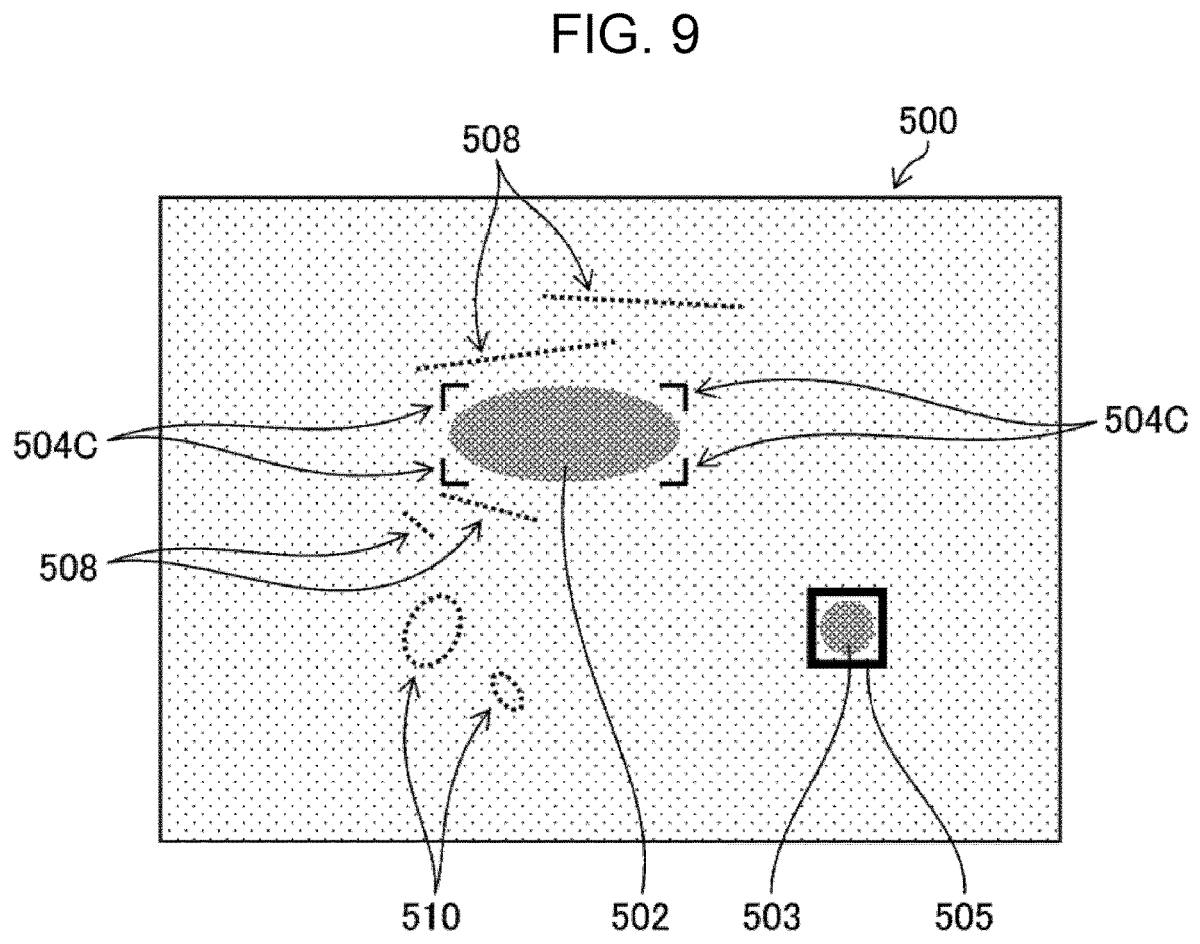

FIG. 9 is a view illustrating an example display in a case where a notification is provided at a notification level corresponding to a positional relationship (distance) between a target object and drawing information. The ultrasound image 500 includes regions of interest 502 and 503. A plurality of measurement lines 508 (drawing information) and a plurality of geometric shapes 510 (drawing information) are drawn near the region of interest 502, and the region of interest 503 is far from these pieces of drawing information. The distinguishability of these pieces of drawing information may affect a recognition result of a target object, and can be considered to more greatly affect the region of interest 502, which is closer to the pieces of drawing information, than the region of interest 503. In the example in FIG. 9, the width of the lines of a bounding box 505 for the region of interest 503 is increased to increase the relative notification level, and the width of the lines of a bounding box 504C for the region of interest 502 is decreased, with only the corner portions thereof visible to decrease the relative notification level. In this manner, the notification level is determined on the basis of the positional relationship (distance) between the target object and the drawing information, thereby making it possible to provide an appropriate notification in accordance with the distinguishability of the drawing information.

Applications to Other Medical Images

In the first embodiment described above, a description has been given of recognition using an ultrasonic endoscopic image, which is one aspect of a medical image (image for medical use). However, the medical image processing apparatus, the endoscope system, the medical image processing method, and the medical image processing program according to the present invention are also applicable to the use of medical images other than an ultrasonic endoscopic image, such as an ultrasound image acquired by an ultrasound apparatus (such as a body-surface endoscope apparatus) other than an endoscope and an endoscopic image acquired by an optical endoscope apparatus that captures an image of a subject by using white light and/or special light.

While embodiments and other examples of the present invention have been described, the present invention is not limited to the aspects described above, and various modifications may be made.

REFERENCE SIGNS LIST

- 2 endoscope system
- 10 ultrasound scope
- 12 ultrasonic processor device
- 14 endoscope processor device
- 16 light source device
- 18 monitor
- 20 insertion section
- 20*a* longitudinal shaft
- 22 handheld operation section
- 24 universal cord
- 26 ultrasonic connector
- 28 endoscope connector
- 30 light source connector
- 32 tube
- 34 tube
- 36 air/water supply button
- 38 suction button
- 42 angle knob
- 44 treatment tool insertion port
- 50 tip main body
- 52 bending part
- 54 soft part
- 62 ultrasound probe
- 64 balloon
- 70 water supply tank
- 72 suction pump
- 100 transmitting/receiving unit
- 102 image generation unit

104 CPU
106 target object recognition unit
108 notification level determination unit
110 communication control unit
112 display control unit
114 drawing information acquisition unit
116 drawing information recognition unit
118 memory
120 recording unit
500 ultrasound image
502 region of interest
503 region of interest
504 bounding box
504A bounding box
504B bounding box
504C bounding box
505 bounding box
506 character string
506A character string
508 measurement line
510 geometric shape
600 screen
602 ultrasound image
604 arrow
606 character string
608 measurement line
610 measurement shape
S110 to S250 step of medical image processing method

What is claimed is:

1. A medical image processing apparatus comprising a processor configured to execute:

an image acquisition process for sequentially acquiring time-series medical images;

a drawing information acquisition process for acquiring drawing information drawn in the medical images;

a drawing information recognition process for recognizing the acquired drawing information;

a target object recognition process for recognizing a target object by using a first trained model constructed by machine learning from the medical images, wherein the first trained model is trained by captured images of a living body;

a notification level determination process for determining a notification level the target object by using the recognized drawing information; and a display process for causing a display device to display the target object at the determined notification level, wherein the processor is configured to, in response to the drawing information being recognized in the drawing information recognition process, reduce the notification level to be lower than a notification level when the drawing information is not recognized in the notification level determination process.

2. The medical image processing apparatus according to claim 1, wherein the processor is configured to, in the drawing information acquisition process, acquire the drawing information from a medical imaging apparatus connected to the medical image processing apparatus.

3. The medical image processing apparatus according to claim 1, wherein the processor is configured to, in the drawing information acquisition process, perform image processing on the medical images to acquire the drawing information.

4. The medical image processing apparatus according to claim 3, wherein the processor is configured to, in the drawing information acquisition process, acquire the drawing information by using a second trained model constructed by machine learning.

5. The medical image processing apparatus according to claim 1, wherein the processor is configured to check the medical images against drawable information that is drawable in the medical images to acquire the drawing information.

6. The medical image processing apparatus according to claim 1, wherein the processor is configured to, in the drawing information acquisition process, acquire information related to a geometric shape, a text, or a symbol drawn in the medical images as the drawing information.

7. The medical image processing apparatus according to claim 6, wherein the processor is configured to, in the drawing information acquisition process, acquire at least one of a position, a size, a shape, a line type, a color, or a type of at least one of the geometric shape, the text, or the symbol as the drawing information.

8. The medical image processing apparatus according to claim 1, wherein the processor is configured to reduce the notification level for the target object to be lower than a notification level when the medical images do not have the drawing information, in accordance with an amount of the drawing information.

9. The medical image processing apparatus according to claim 8, wherein the processor is configured to reduce the notification level for a target object for which the amount of the drawing information is recognized to be greater than or equal to a threshold value, such that the notification level is lower than a notification level when the medical images do not have the drawing information.

10. The medical image processing apparatus according to claim 1, wherein the processor is configured to, in response to the drawing information being acquired in the drawing information acquisition process, reduce the notification level for the target object to be lower than a notification level when the medical images do not have the drawing information, regardless of an amount of the drawing information.

11. The medical image processing apparatus according to claim 8, wherein the processor is configured to determine the amount of the drawing information in accordance with at least one of a position, a size, a shape, a line type, a color, or a type of a geometric shape, a text, or a symbol in the medical images.

12. The medical image processing apparatus according to claim 1, wherein the processor is configured to, in the notification level determination process, determine the notification level for the target object on the basis of a positional relationship between the target object and the drawing information in the medical images.

13. An endoscope system comprising:

the medical image processing apparatus according to claim 1;

an endoscope to be inserted into a subject, the endoscope comprising an imaging unit configured to sequentially capture the medical images; and the display device.

14. The endoscope system according to claim 13, wherein the endoscope is an ultrasonic endoscope configured to acquire ultrasound images of the subject as the medical images.

15. A medical image processing method executed by a medical image processing apparatus comprising a processor, the medical image processing method comprising:

an image acquisition step of sequentially acquiring time-series medical images;

a drawing information acquisition step of acquiring drawing information drawn in the medical images;

a drawing information recognition step of recognizing the acquired drawing information;

a target object recognition step of recognizing a target object by using a first trained model constructed by machine learning from the medical images, wherein the first trained model is trained by captured images of a living body;

a notification level determination step of determining a notification level for the target object by using the recognized drawing information; and a display step of causing a display device to display the target object at the determined notification level, wherein in response to the drawing information being recognized in the drawing information recognition step, reduce the notification level to be lower than a notification level when the drawing information is not recognized in the notification level determination step.

16. A non-transitory, computer-readable tangible recording medium which stores a program for causing, when read by a computer, the computer to execute the medical image processing method according to claim 15.

* * * * *